United States Patent
Gleichauf et al.

(10) Patent No.: US 7,381,385 B2
(45) Date of Patent: *Jun. 3, 2008

(54) STERILE CONTAINER

(75) Inventors: Wilhelm Gleichauf, Tuttlingen-Moehringen (DE); Mariana Jakab, Tuttlingen (DE); Friedrich-Wilhelm Oertmann, Tuttlingen (DE); Torsten Renner, Eisenberg (DE); Stefan Schuster, Tuttlingen (DE); Wolfgang Schwanke, Rietheim-Weilheim (DE)

(73) Assignee: AESCULAP AG & Co. KG, Tuttlingen (DE)

( * ) Notice: Subject to any disclaimer, the term of this patent is extended or adjusted under 35 U.S.C. 154(b) by 602 days.

This patent is subject to a terminal disclaimer.

(21) Appl. No.: 10/846,853

(22) Filed: May 13, 2004

(65) Prior Publication Data

US 2004/0256270 A1 Dec. 23, 2004

Related U.S. Application Data

(63) Continuation of application No. PCT/EP02/12670, filed on Nov. 13, 2002.

(30) Foreign Application Priority Data

Nov. 15, 2001 (DE) ............................. 101 56 937

(51) Int. Cl.
*A61L 2/20* (2006.01)
*A61L 2/07* (2006.01)
(52) U.S. Cl. ...................... 422/300; 422/297
(58) Field of Classification Search .............. None
See application file for complete search history.

(56) References Cited

U.S. PATENT DOCUMENTS

| 4,129,908 | A | | 12/1978 | Wagner | |
|---|---|---|---|---|---|
| 4,661,326 | A | * | 4/1987 | Schainholz | 422/310 |
| 4,704,254 | A | * | 11/1987 | Nichols | 422/310 |
| 4,728,504 | A | | 3/1988 | Nichols | |
| 4,748,003 | A | * | 5/1988 | Riley | 422/112 |
| 5,176,884 | A | | 1/1993 | Taschner et al. | |
| 5,183,643 | A | | 2/1993 | Nichols | |
| 5,202,098 | A | | 4/1993 | Nichols | |
| 5,324,489 | A | | 6/1994 | Nichols et al. | |
| 5,346,075 | A | * | 9/1994 | Nichols et al. | 211/60.1 |
| 5,352,416 | A | | 10/1994 | Wagner | |
| 5,968,459 | A | * | 10/1999 | Nalepa et al. | 422/300 |
| 6,889,832 | B2 | * | 5/2005 | Gabele | 206/370 |
| 6,994,128 | B2 | * | 2/2006 | Gleichauf et al. | 141/326 |

(Continued)

FOREIGN PATENT DOCUMENTS

DE 12 17 551 5/1966

(Continued)

*Primary Examiner*—E. Leigh McKane
(74) *Attorney, Agent, or Firm*—Lipsitz & McAllister, LLC (57) ABSTRACT

The invention relates to a sterile container, especially for receiving and storing surgical instruments or material in sterile conditions, comprising and receiving area formed by a container bottom and container walls, a lid for sealing the receiving area, and a gas exchange opening which can be sealed by a sterile filter. In order to enable the sterile filter to be replaced in a simple manner, a filter unit is provided, comprising the sterile filter, a support and a holding element, the sterile filter is maintained between the support and the holding element and the filter unit is mounted on the lid and/or bottom of the container.

26 Claims, 8 Drawing Sheets

U.S. PATENT DOCUMENTS

| | | | |
|---|---|---|---|
| 7,172,740 B2 * | 2/2007 | Gleichauf et al. | 422/300 |
| 2002/0098138 A1 | 7/2002 | Gabele | |

FOREIGN PATENT DOCUMENTS

| | | |
|---|---|---|
| DE | 34 07 112 | 9/1985 |
| DE | 34 38 463 | 4/1986 |
| DE | 37 11 621 | 10/1987 |
| DE | 41 25 673 | 7/1992 |
| DE | 41 11 077 | 10/1992 |
| WO | 99/27969 | 6/1999 |
| WO | 00/12141 | 3/2000 |
| WO | 01/08583 | 2/2001 |
| WO | WO 01/78619 A1 * | 10/2001 |

* cited by examiner

STERILE CONTAINER

The present disclosure relates to the subject matter disclosed in international application PCT/EP02/12670 of Nov. 13, 2002, which is incorporated herein by reference in its entirety and for all purposes.

BACKGROUND OF THE INVENTION

The invention relates to a sterile container, in particular for the holding and sterile storage of surgical instruments or material, comprising a holding space, which is defined by a container base and container walls, a lid for closing the holding space and a gas exchange opening, which can be closed off by a sterile filter.

Sterile containers of this type are, for example, loaded with surgical instruments or material and sterilized in a sterilizer. A sterile filter is required in order to prevent germs from penetrating into the container. The sterile filter has to be replaced from time to time, which in previously known sterile containers has only been possible in laborious manner.

Therefore, it is an object of the present invention to improve a sterile container of the type described in the introduction in such a way that the sterile filter is easy to exchange.

SUMMARY OF THE INVENTION

In a sterile container of the type described in the introduction, this object is achieved, according to the invention, by virtue of the fact that there is a filter unit, which comprises the sterile filter, a carrier and a holding element, that the sterile filter is held between the carrier and the holding element, and that the filter unit is mounted on the lid and/or on the container base.

To exchange the sterile filter, it is sufficient to release the complete filter unit from the lid or from the container base and exchange it. There is no longer any need to grip the sterile filter itself, which on the one hand helps to avoid damage to it and on the other hand prevents soiling.

In a preferred embodiment of the invention, it is possible to provide that the filter unit is configured in the form of a single-part filter cartridge, and that the carrier, the sterile filter, and the holding element are nonreleasably connected to one another. This allows the filter unit to be exchanged as a whole, making filter exchange a quicker operation. At the same time, the sterile filter can be permanently mounted and protected in the filter cartridge. Furthermore, the leaktightness of the filter cartridge can be tested even during production. This is not always ensured in the case of a manually assembled filter unit.

To securely hold the sterile filter, it is advantageously provided that the carrier has at least one carrier support for supporting the sterile filter, and at least one carrier aperture which borders on the carrier support. While the carrier support on the one hand stabilizes the sterile filter of the filter unit, the carrier aperture allows sufficient gas exchange through the sterile filter.

To protect the sterile filter from mechanical loads, in particular to protect it from damage from instruments and tools acting in or on the sterile container, there is preferably at least one carrier aperture cover which covers the at least one carrier aperture at a spacing therefrom.

It may be advantageous if the filter unit is mounted moveably, if the filter unit, in a closed position, closes a flow path and, in a flow-permitting position, opens the flow path, so that gas exchange in the closed position is possible only through the sterile filter and in the flow-permitting position is possible through the sterile filter and/or through the flow channel. The moveable mounting allows gas exchange to be additionally controlled and/or regulated. In particular if relatively high levels of gas exchange are required, the filter unit can be transferred into the flow-permitting position and an additional flow path can be opened up.

To allow the objects stored in the sterile container to be stored in the complete absence of germs, the filter unit, in the closed position, is held on the sterile container under prestress.

It is expedient if there is a sealing element for mounting the filter unit in a gastight manner. This sealing element allows the filter unit to be completely sealed on the sterile container.

It is particularly expedient if the sealing element comprises a sealing ring mounted on the holding element. Sealing rings are particularly simple to produce and are also simple to fit to the holding element or another element of the filter unit.

According to a preferred embodiment of the invention, it is advantageous if there is a pressure-relief valve, if the pressure-relief valve is disposed in such a way that in a basic position it adopts a closed position and that it adopts a flow-permitting position when a pressure in the vicinity of the sterile container exceeds a pressure in the sterile container by a predetermined pressure difference. This makes it possible to avoid damage to the sterile container, since, before the sterile container can be deformed as a result of a particularly high pressure in the surrounding region or a correspondingly high pressure gradient, the pressure-relief valve opens, allowing gas to flow into the container.

To reduce the number of components required, it is advantageous if the filter unit forms the pressure-relief valve. The filter unit therefore performs two functions; firstly it serves to block germs, and secondly it serves as a pressure-relief valve.

It is particularly expedient if the filter unit is mounted on an inner side of the lid. This creates additional space in the container. Moreover, it is also possible to exchange a filter unit by exchanging a complete lid. Mounting on the inner side of the lid offers additional protection for the filter unit with respect to mechanical load or damage.

To additionally protect the filter unit against mechanical damage, it may be advantageous to provide a protective element which covers the filter unit at a spacing therefrom.

It is advantageous if the protective element is disposed on an outer side of the lid. This means that the sterile filter is securely mounted between the protective element and the carrier.

To achieve simple assembly or to allow simple access to the filter unit, it is possible to provide that the protective element can be connected to the lid by means of a snap-action or latching connection.

To avoid further openings at the lid, it is advantageous if the protective element can be latched to an inner rim of the gas exchange opening. The gas exchange opening is in any event required in order to allow gas exchange with the interior of the sterile container.

A particularly simple latching connection results if the protective element comprises elastic spring arms which protrude toward the sterile container and are provided with a latching projection. Apart from the spring arms, there is no need for any moveable parts for fixing the protective element to the sterile container.

It is advantageously possible for there to be between the protective element and the lid at least one opening for the passage of gas, which is in fluid communication with the gas exchange opening and is disposed in such a way that gas flow is made possible in a direction of flow running substantially transversely with respect to the flow-permitting direction of the sterile filter. Gas exchange from the region surrounding the sterile container to the gas exchange opening can be achieved via the opening for the passage of gas, which is necessary in particular if the protective element is disposed on the lid.

To prevent liquid from penetrating into the filter unit, it is expedient if there is an inflow edge, which is disposed on the outer side of the lid, faces away from the gas exchange opening and slopes downward toward the outside relative to a lid plane. If liquid reaches the lid, the inclination of the inflow edge means that it can flow away from the gas exchange opening and therefore cannot reach the filter unit.

Preferably, the lid has at least one spacer element for stacking a further sterile container on the sterile container, so that gas exchange through the gas exchange opening is possible with stacked sterile containers. On the one hand, therefore, this allows gas exchange, and on the other hand the gas exchange opening and the sterile filter covering it are also protected from further sterile containers placed on top of them.

According to a preferred embodiment of the invention, it is possible to provide for the sterile filter to be a long-term filter, in particular made from polytetrafluoroethylene (PTFE). This makes it possible to extend the intervals between maintenance on the sterile container. It is only seldom necessary to exchange the filter unit.

The sterile container becomes particularly expedient and simple to produce if the lid is made from a plastic, in particular from polyether ether ketone (PEEK) or polyphenylene sulfone (PPSU).

BRIEF DESCRIPTION OF THE DRAWINGS

The following description of a preferred embodiment of the invention, in conjunction with the drawing, serves to provide a more detailed explanation. In the drawing.

DETAILED DESCRIPTION OF THE INVENTION

Figure 1:
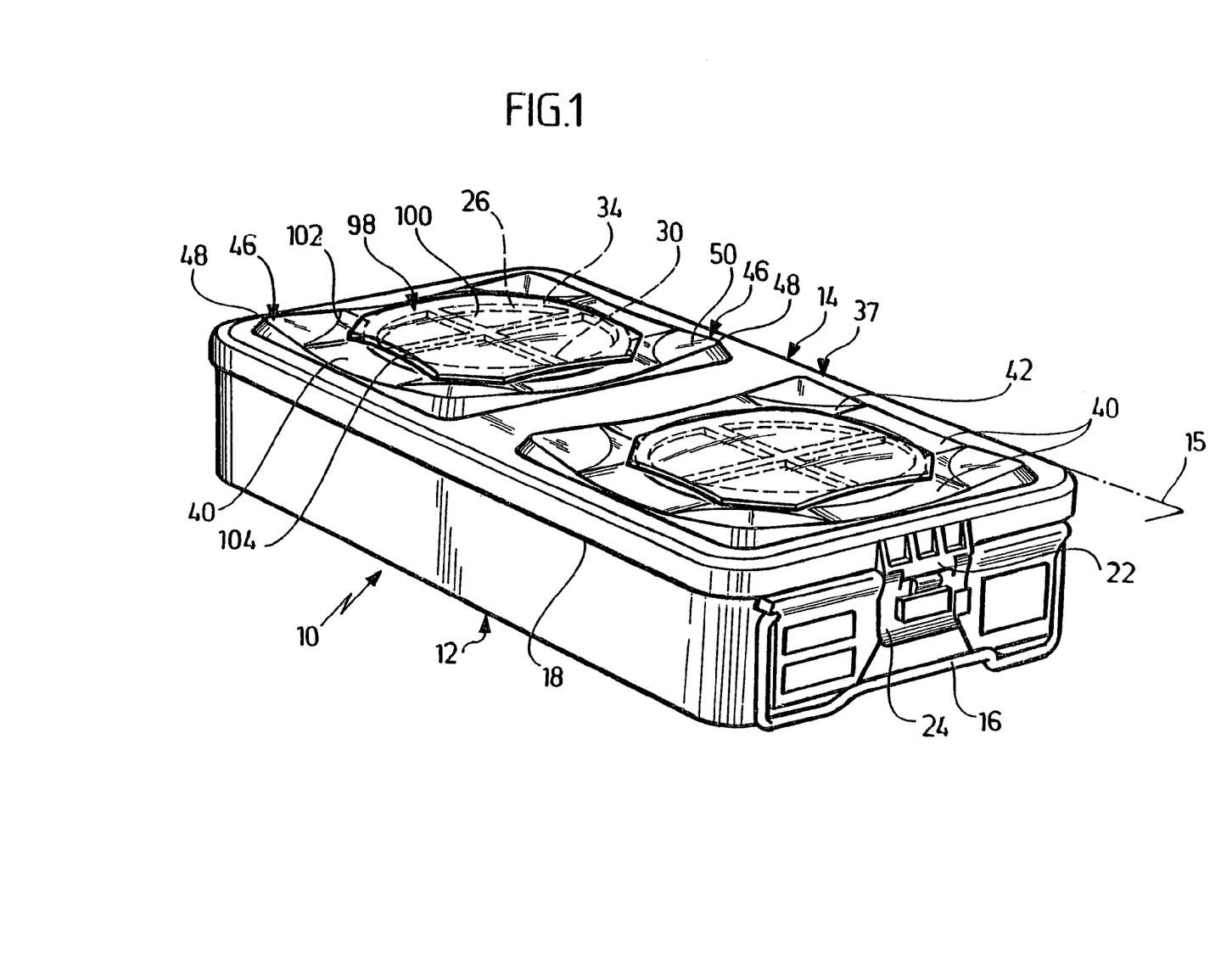
FIG. 1 shows a perspective overall view of a sterile container.

FIG. 1 illustrates a sterile container, which is denoted overall by reference numeral 10 and comprises a substantially tub-like, cuboidal container 12 for holding, for example, surgical instruments or material, and a lid 14. Pivotably mounted carry handles 16 are disposed at the end faces of the container 12.

The structure of the lid 14 is explained in more detail with reference to FIGS. 2 to 9.

The lid 14 is provided with an encircling rim 18 which projects perpendicularly from a lid plane 15, so that the lid 14 completely covers and partially engages around the container 12. A sealing rim 20, between which and the rim 18 a seal (not shown) can be inserted, runs parallel to and at a spacing from the rim 18. When the lid 14 has been fitted, the sealing rim 20 is located inside the container 12. The seal makes it possible to produce a gastight connection between the lid 14 and the container 12.

At its narrow end sides, the lid 14 in each case has a bearing bracket 22, on which a resilient closure flap 24 can pivot about a pivot axis running parallel to a pivot axis of the carry handle 16 when the lid 14 is seated on the container 12.

The lid 14 has two symmetrically disposed circular openings 26, which have an opening rim 28 which faces parallel to the lid plane 15 and on which four webs 30, which run perpendicularly toward one another and meet in the center of the opening 26, for stiffening the lid, are disposed symmetrically. Between each pair of webs 30 disposed at the opening rim 28, two indentations 32 and 33 are cut symmetrically into the opening rim 28.

The opening 26 is surrounded by an annular surface 34, which runs parallel to the lid plane 15 but is set back toward an underside 36 of the lid. As a result, an inner annular edge 38 is formed on a top side 37 of the lid and an outer annular edge 39 is formed on the underside 36 of the lid.

Four inflow edges 40 and four support surfaces 42 border the annular edge 38 alternately one after the other. The inflow edges 40 are curved concavely away from the lid top side 37 and are inclined outward, so that an inclined plane with an angle of inclination 44 between the inflow edge 40 and the lid plane 15 of approximately 2° is formed.

The support surfaces 42 run parallel to the lid plane 15 and, when seen in plan view, are approximately in the shape of a trapezoid, but in each case with concavely curved base edges. The longer of the two base lines of the support surface 42 is adjoined by a three-sided pyramid 46, which has a base area which is substantially in the shape of an isosceles right-angled triangle. An apex 48 of the pyramid lies just above the base sides, which intersect at right angles, of the base surface, slightly offset toward the opening 26.

This results in the formation of a run-off surface 50 which is approximately in the shape of an isosceles, right-angled triangle which is inclined toward the support surface 42. The support surface 42 is offset away from the lid top side 37, parallel to the lid plane 15.

The overall result, therefore, is an approximately square structure on the lid 14, which is formed by four pyramids 46, which are each seated in the corners of the square, the side faces of the square running parallel to sides of the lid 14. The inflow edges 40 are therefore inclined perpendicularly toward the sides of the lid 14. The structure has a total of two planes of symmetry running parallel to the sides of the lid 14. On its side facing away from the opening 26, the inflow edge 40 extends down to the level of the lid plane 15. When the lid is seen from the side, therefore, the result is approximately a concave shape, facing away from the lid top side 37, from the apex 48 of the pyramid 46 in a corner of the square structure to the apex 48 of the pyramid 46 in an adjacent corner of the structure.

Adjacent to the indentations 32 and 33 are disposed a total of four hollow-cylindrical, open sleeves 52 protruding from the underside 36 of the lid. A filter cartridge 54 is mounted resiliently on these sleeves. The filter cartridge comprises an approximately octagonal filter holder 58, which is provided with a carrier rim 56 and has an annular filter receiver 60 for accommodating a circular long-term filter 62. An annular recess 64, which is configured with a larger diameter than the filter receiver 60, is used to accommodate a holding ring 66, which in cross-section has an L-shaped profile, one limb of which presses the long-term filter 62 into the filter receiver 60 and the other limb of which engages against the recess 64. The holding ring 66 is provided with an annular ring groove, which in cross-section includes slightly more than half of a circle, for accommodating a sealing ring 70.

Four mounting sleeves 74, corresponding to the sleeves 52 disposed on the lid 14, protrude from a filter holder base 72 toward the lid; these mounting sleeves are open from the filter holder base 72, and their other, closed end face 76 is provided with a central through opening 78 whose diameter corresponds to that of the sleeve 52. To mount the filter cartridge 54, the four mounting sleeves 74 are pushed over the sleeves 52, a coil spring 80 is in each case fitted over the sleeves 52, and then the mounting sleeves 74 are closed off by the filter holder base 72 with a stopper 82 which has a disk-like head 84 whose external diameter is matched to the internal diameter of the mounting sleeves 74. On account of the fact that the coil spring 80 is supported against the head 84 of the stopper 82, it presses the end face 76 onto the underside 36 of the lid.

The filter holder base 72 is provided with a total of twenty strip-like slots 86 of different lengths, with in each case five slots running parallel to one another and approximately covering the area of a quarter-circle. Slots 86 belonging to adjacent quarter-circles are in each case positioned perpendicular to one another. A protective web 88 is formed between each pair of slots 86. A strip 90, which faces away from the filter holder base 72 and from which, once again running parallel to the filter holder base 72, there protrudes a support web 92 facing away from the associated protective web 88 and in each case completely covering a slot 86, is disposed on each protective web 88. All the support webs 92 define a common plane on which the long-term filter 62 rests. Overall, the filter receiver 60 and the support webs 92 form a carrier support for supporting the long-term filter 62.

The filter holder 58, the long-term filter 62 and the holding ring 66 are fixedly connected to one another, for example by welding or adhesive bonding. In the assembled state, the coil springs 88 press the filter cartridge 54 onto the underside 36 of the lid, with the filter cartridge 54 being sealed against the underside 36 of the lid by means of the sealing ring 70.

The holding ring 66 has an outer ring and an inner ring 94 running concentrically therewith, from which four holding ring webs 96 disposed radially and symmetrically stabilize the holding ring 66.

On account of the offset arrangement of support web 92 and protective web 88, the long-term filter 62 supported on the support webs 92 is protected from direct mechanical damage. However, the long-term filter 62 is virtually unprotected on its side facing toward the opening 26. For this purpose, a protective cover 98, which is of mirror-symmetrical configuration and has a cover surface 100 curved convexly away from the top side 37 of the cover, is provided as a protective element; when the cover surface 100 is seen in plan view, it is in the shape of a non-equilateral octagon with short sides 102 and long sides 104.

An annular strip 108, which comprises four cutouts 110, each disposed diametrically in pairs, protrudes from an underside 106 of the protective cover. These cutouts 110 are shaped in such a manner that they can engage over the webs 30 and the protective cover 98 rests on the webs 30. Two spacer strips 112, which cross one another, are disposed on the underside 106 of the protective cover, as additional spacers, which spacer strips, in the region of the cutouts 110, project outward beyond the ring strip 108 as far as the long sides 104. When the protective cover 98 has been fitted, these strips rest on the annular surface 34.

To secure the protective cover 98 there are four latching connectors 114, which each comprise three limbs, which are disposed at right angles to one another, form a U-shaped frame 116 and two of which protrude radially outward from the ring strip 108. As free ends of the spacer strips 112, they form spacers resting on the annular surface 34. From a transverse web 118 of the frame 116, two latching arms 120 protrude parallel and at right angles from the underside 106 of the protective cover, which latching arms are provided at their free ends with a latching lug 122 protruding at right angles. The four latching connectors 114 are disposed in diametrically opposite pairs on the protective cover 98.

To secure the protective cover 98, the latter is moved perpendicularly toward the top side 37 of the lid and is oriented in such a way that the cutouts 110 each face toward a web 30 and the latching arms 120 each slide into one of the two indentations 32 and 33. As soon as the cutouts 110 rest on the webs 30, the closure strips 112 and the frames 116 rest on the annular surface 34, the latching arms 120 latch to the opening rim 28 as a result of the latching lugs 122 engaging behind the opening rim 28.

The size of the protective cover 98 is selected to be such that in the inserted position the annular surface 34 is completely covered. The short sides 102 then rest on the support surfaces 42, while the long sides 104 run parallel to the side edges of the lid 14 and in each case partially cover the inflow edges 40. When the protective cover 98 is inserted, the long-term filter 62 held in the filter cartridge 54 is also completely protected from mechanical damage from its other side.

Figure 2:
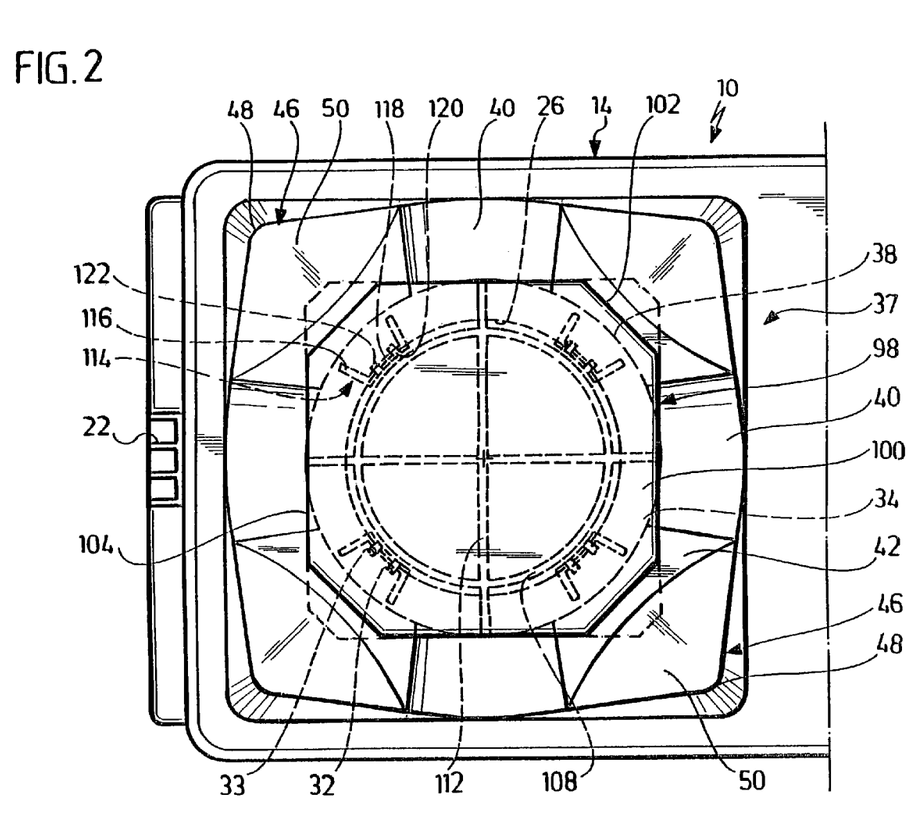
FIG. 2 shows a plan view of an excerpt of a sterile container.
Figure 3:
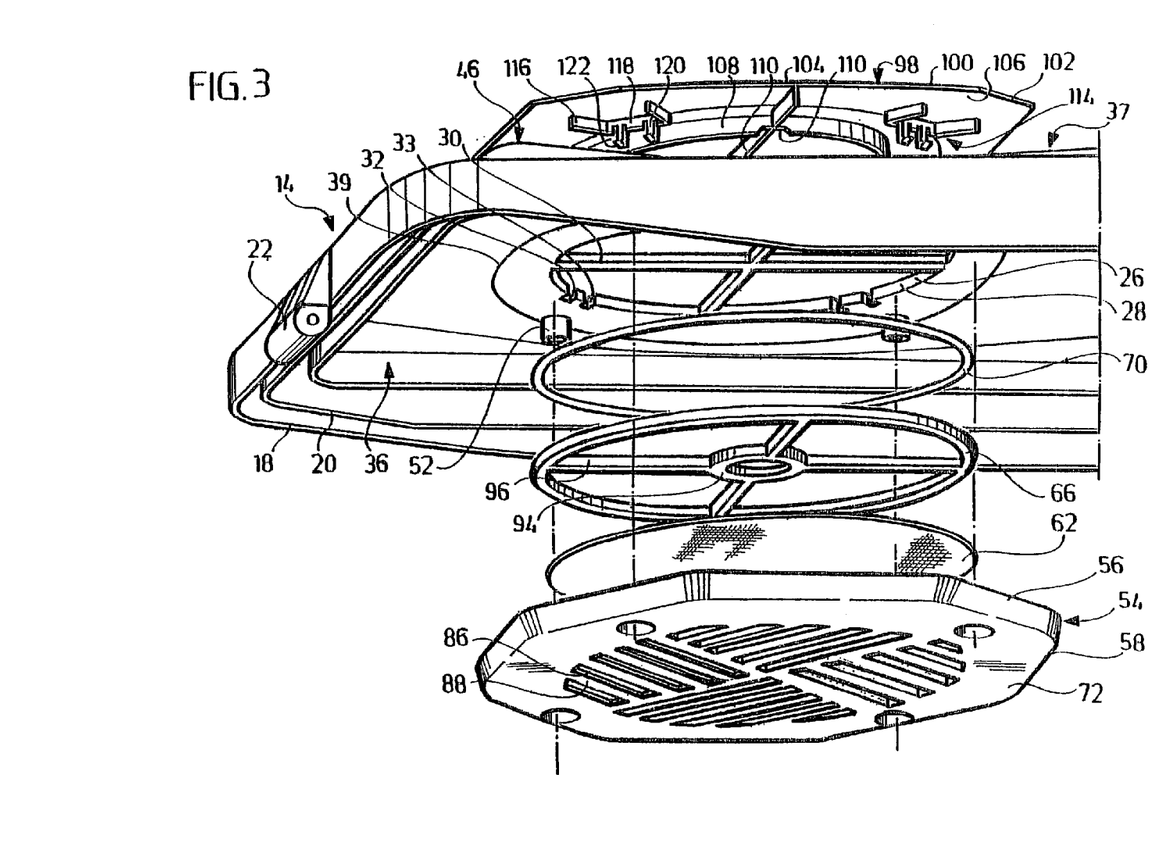
FIG. 3 shows an exploded view of an excerpt of a lid of the sterile container.
Figure 4:
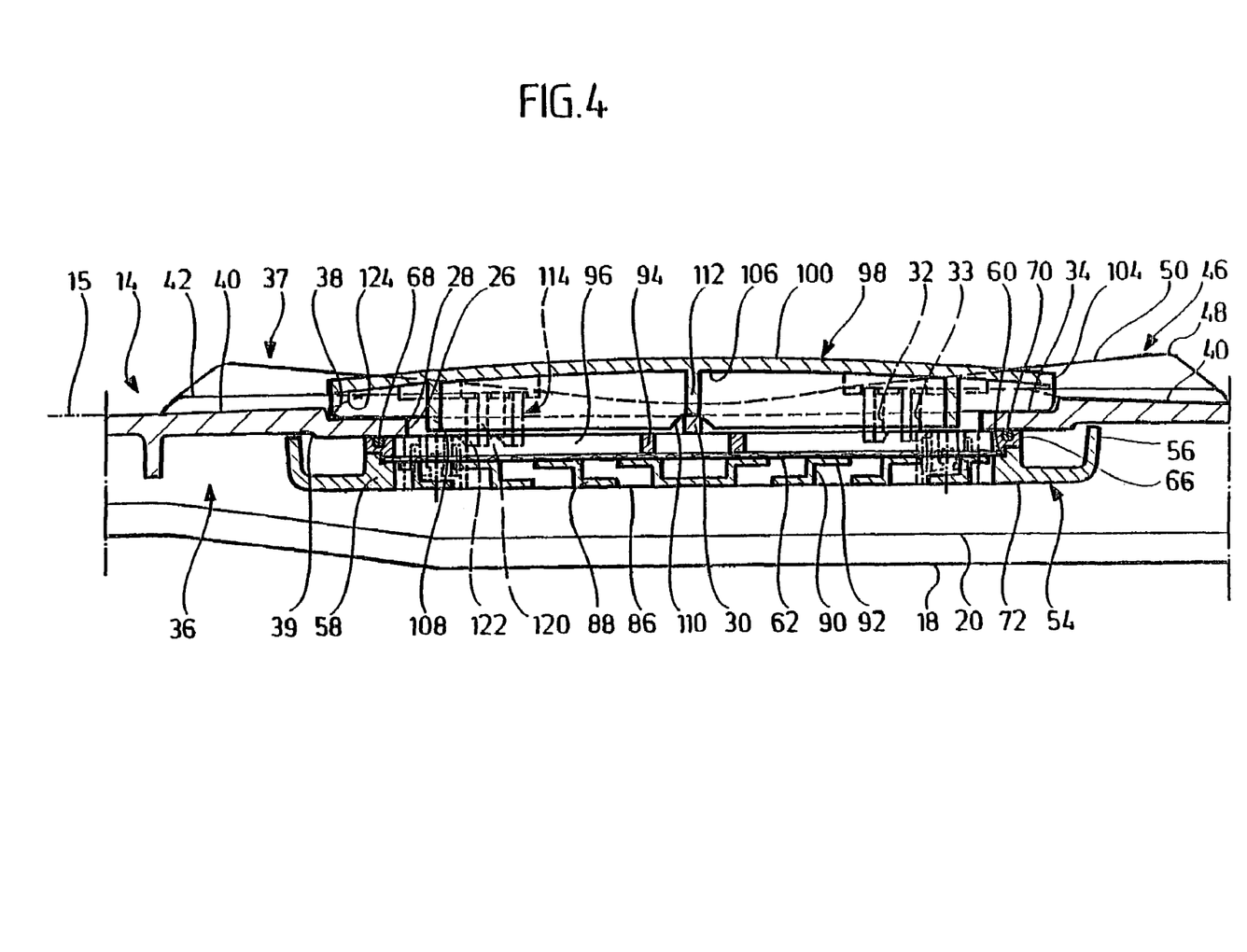
FIG. 4 shows a partially cut-away cross-sectional view through an excerpt of a lid.
Figure 5:
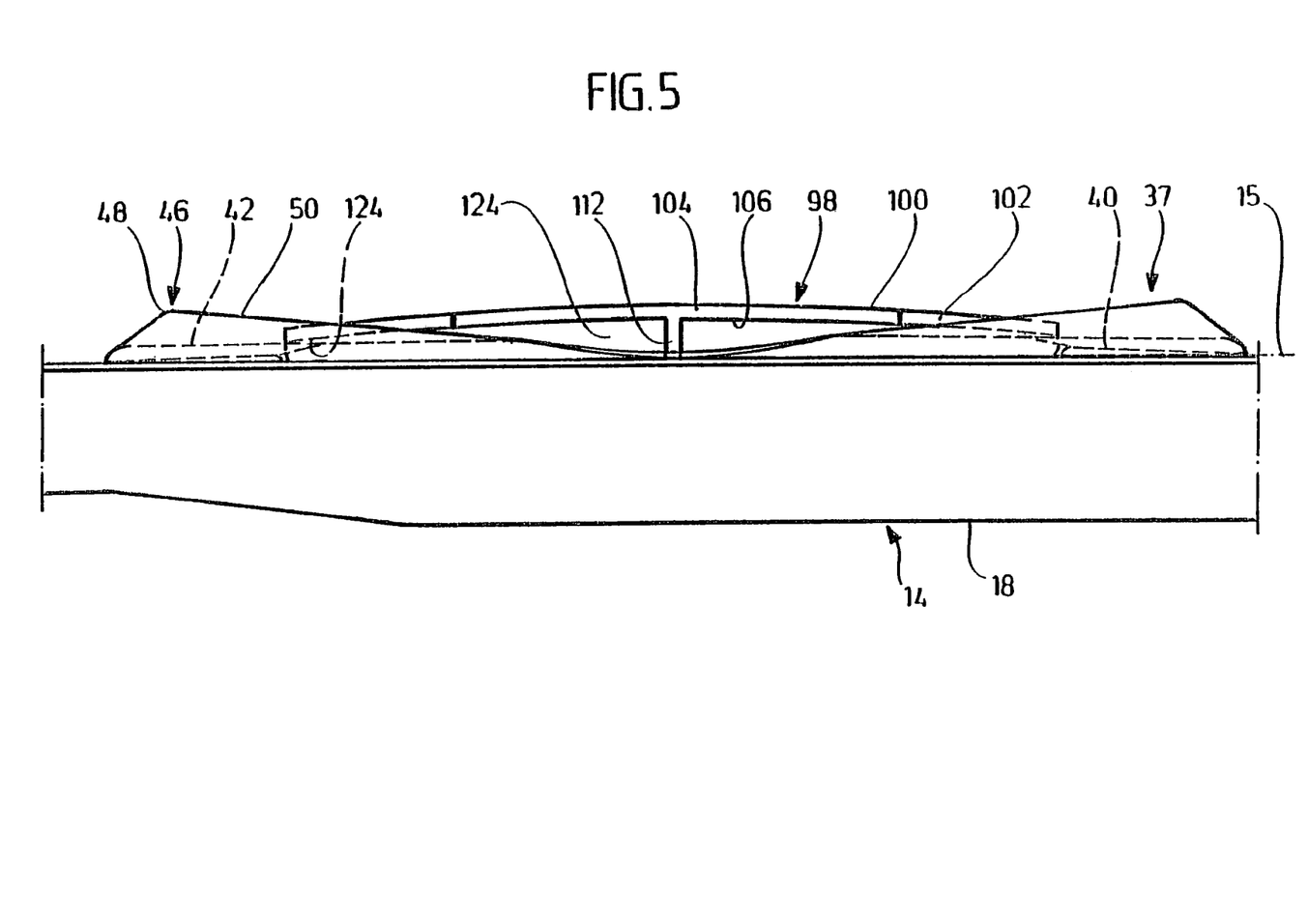
FIG. 5 shows a partially cut-away side view of an excerpt of a lid.
Figure 6:
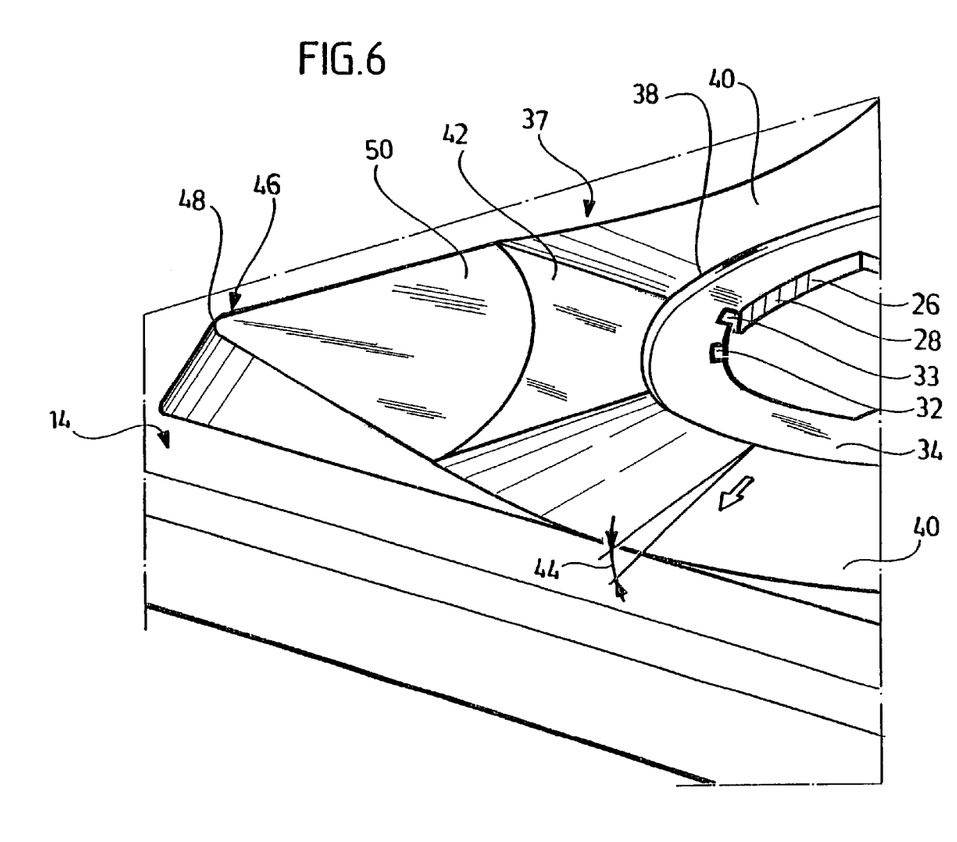
FIG. 6 shows an enlarged, perspective partial view of a lid.
Figure 7:
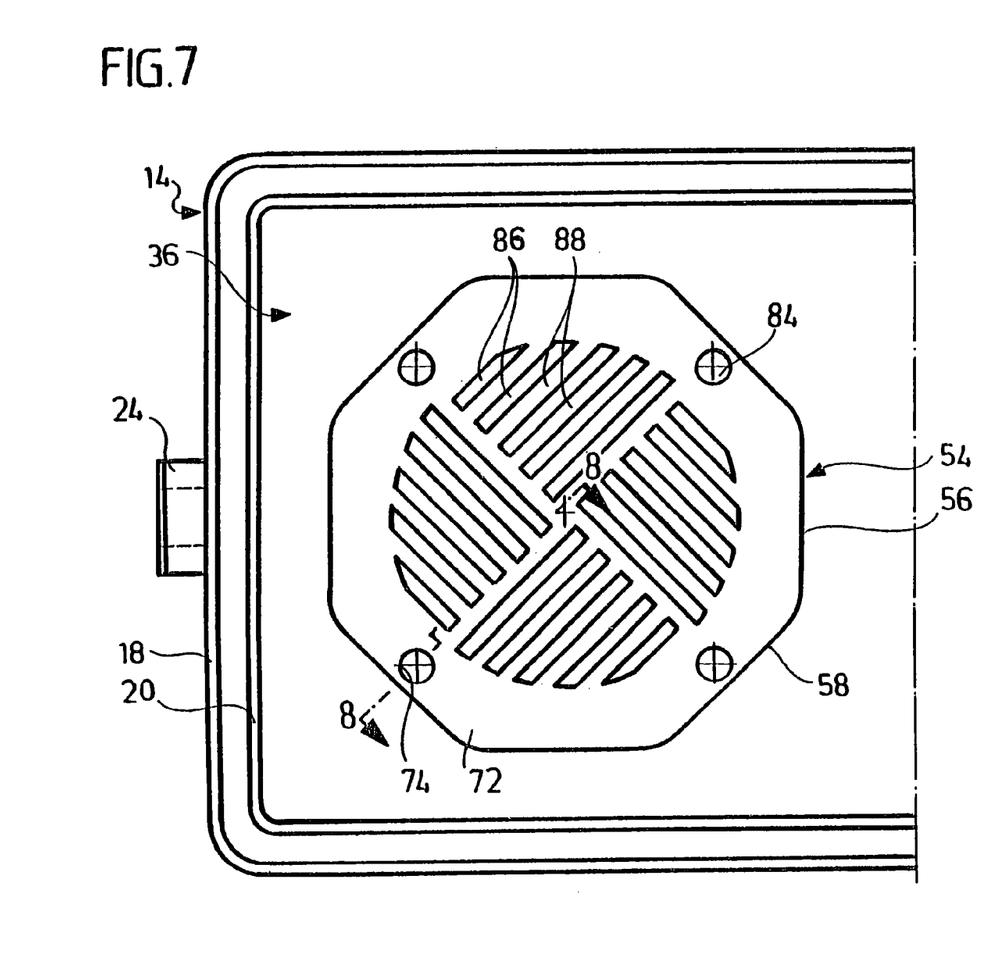
FIG. 7 shows a plan view onto the underside of half of a lid.

In an alternative variant of a lid, which is indicated by dot-dashed lines in FIG. 2, the long sides 104 of the protective cover 98 are lengthened. The pyramid 46 then has, in its run-off surface 50, an additional recess, in which the short side 102 of the protective cover 98 is fitted. This results in a seamless transition between the run-off surface 50 and the cover surface 100.

The highest point of the protective cover 98 when the latter is inserted lies beneath the highest point of the four pyramids 46, so that when sterile containers 10 are stacked on top of one another the container 12 which is mounted on the lid 14 rests only on the apexes 48 of the pyramids 46 but does not touch the protective covers 98.

If, with a substantially horizontally mounted sterile container 10, liquid reaches the top side 37 of the lid, for example reaches the protective cover 98, the curvature of the protective cover 98 means that the liquid can flow off to the short or long sides 102 or 104, respectively. From the long sides 104, the liquid passes onto the inflow edges 40, from which the liquid can flow off to the sides of the lid 14 on account of the inclination of these edges.

When the protective cover 98 is fitted, a substantially double-convex lens-shaped inflow opening 124, as seen in side view, is formed, through which a gaseous fluid can flow in and out. The fluid then flows substantially parallel to the lid plane 15, through the opening 26 substantially perpendicular thereto. In a basic position illustrated in FIG. 8, the filter cartridge 54 engages against the underside 36 of the lid, sealed off by means of the sealing ring 70. If the sterile container 10 is exposed to hot steam, the latter flows to the long-term filter 62, as described above. It passes through the long-term filter 62 and then follows a flow channel, defined by the support web 92, the strip 90 and the protective web 88, into the interior of the container 12.

Figure 8:
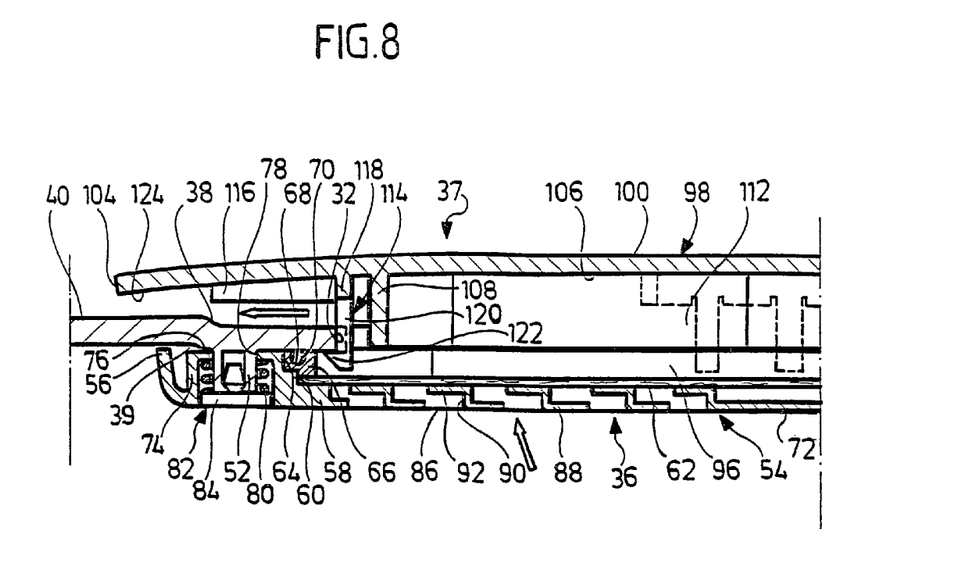
FIG. 8 shows a cross-sectional view of an excerpt of a filter cartridge which is mounted in a gastight manner on the lid.
Figure 9:
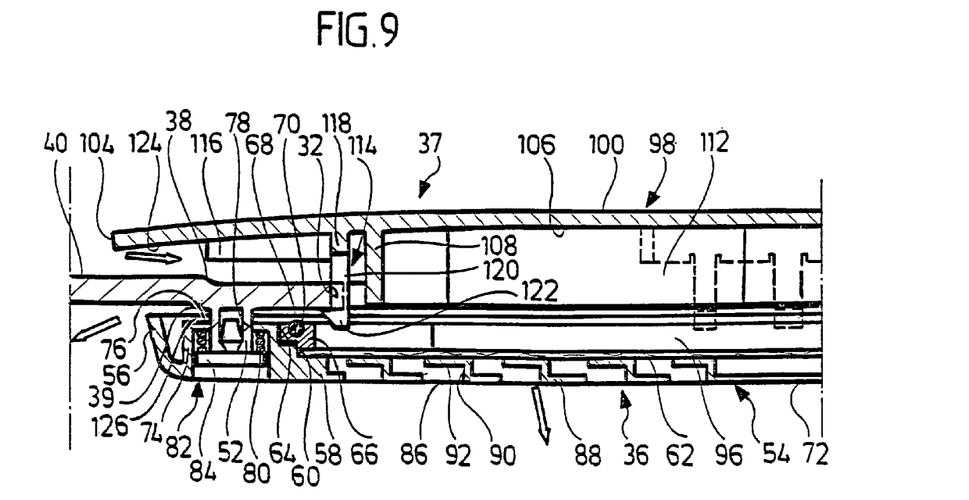
FIG. 9 shows a cross-sectional view of an excerpt similar to that shown in FIG. 8, with a filter cartridge lifted off.

If a pressure acting outside on the sterile container 10 exceeds a force which can be set by means of the coil springs 80, the filter cartridge 54, which is mounted resiliently on the lid 14, acts as a pressure-relief valve. The filter cartridge 54 is lifted off the underside 36 of the lid and opens up a flow channel 126 which is closed in the basic position, as illustrated in FIG. 9. Hot steam can now pass not only through the long-term filter 62 but also into the interior of the container 12 via the flow channel 126. As soon as the pressure gradient drops again, the coil springs 80 press the filter cartridge 54 back onto the underside of the lid, so that steam or gas can only flow in and out via the long-term filter 62. FIGS. 8 and 9 use arrows to indicate the incoming and outgoing flow of a gas or steam.

The container 12 may optionally made from metal or plastic. The lid 14 is preferably made completely from a plastic, for example from polyether ether ketone or polyphenylene sulfone. The long-term filter is preferably made from polytetrafluorethylene.

The invention claimed is:

1. A sterile container, comprising:
   a holding space defined by a container base and container walls,
   a lid for closing the holding space,
   a gas exchange opening, and
   a filter unit comprising a carrier and a holding element for holding a sterile filter therebetween,
   said gas exchange opening adapted to be closed off by the sterile filter, the filter unit being mountable on one of the lid and the container base, and being configured in the form of a single-part filter cartridge,
   the carrier, the sterile filter, and the holding element being nonreleasably connectable to one another, and
   the carrier having at least one carrier support for supporting the sterile filter and at least one carrier aperture which adjoins the carrier support.

2. A container according to claim 1, comprising at least one carrier aperture cover which covers the at least one carrier aperture at a spacing therefrom.

3. A container according to claim 1, wherein the filter unit is mounted moveably and, in a closed position, closes a flow path and, in a flow-permitting position, opens the flow path, so that gas exchange in the closed position is possible only through the sterile filter and in the flow-permitting position is possible through at least one of the sterile filter and the flow path.

4. A container according to claim 1, further comprising a sealing element for mounting the filter unit in a gastight manner.

5. A container according to claim 4, wherein the sealing element comprises a sealing ring mounted on the holding element.

6. A container according to claim 1, further comprising:
   a pressure-relief valve, disposed in such a way that in a basic position it adopts a closed position and that it adopts a flow-permitting position when a pressure in the vicinity of the sterile container exceeds a pressure in the sterile container by a predetermined pressure difference.

7. A container according to claim 6, wherein the pressure-relief valve comprises the filter unit.

8. A container according to claim 1, wherein the filter unit is mounted on an inner side of the lid.

9. A container according to claim 1, further comprising a protective element which covers the filter unit at a spacing therefrom.

10. A container according to claim 9, wherein the protective element is disposed on an outer side of the lid.

11. A container according to claim 9, wherein the protective element is adapted to be connected to the lid by means of a snap-action or latching connection.

12. A container according to claim 9, wherein the protective element is adapted to be latched to an inner rim of the gas exchange opening.

13. A container according to claim 9, wherein the protective element comprises elastic spring arms which protrude toward the sterile container and are provided with a latching projection.

14. A container according to claim 9, wherein between the protective element and the lid there is at least one opening for the passage of gas, which opening is in fluid communication with the gas exchange opening and is disposed in such a way that gas flow is made possible in a direction of flow running substantially transversely with respect to a flow-permitting direction of the sterile filter.

15. A container according to claim 1, further comprising an inflow edge, disposed on an outer side of the lid, facing away from the gas exchange opening and sloping downward toward an outside relative to a lid plane.

16. A container according to claim 1, wherein the lid has at least one spacer element for stacking a further sterile container on the sterile container, so that gas exchange through the gas exchange opening is possible with stacked sterile containers.

17. A container according to claim 1, wherein the sterile filter is a long-term filter made from polytetrafluoroethylene (PTFE).

18. A container according to claim 1, wherein the lid is made from a plastic.

19. A container according to claim 18, wherein the lid is made from one of polyether ether ketone (PEEK) or polyphenylene sulfone (PPSU).

20. A sterile container, comprising:
   a holding space defined by a container base and container walls,
   a lid for closing the holding space
   a gas exchange opening, which can be closed off by a sterile filter, and
   a filter unit comprising a carrier and a holding element for holding the sterile filter therebetween, the filter unit:
      (i) being configured in the form of a single-part filter cartridge with the carrier, sterile filter and holding element being nonreleasably connectable to one
      (ii) being moveably mountable to one of the lid and the container base,
      (iii) in a closed position, closing a flow path and,
      (iv) in a flow-permitting position, opening the flow path,
   so that gas exchange in the closed position is possible only through the sterile filter and in the flow-permitting position is possible through at least one of the sterile filter and the flow path.

21. A container according to claim 20, wherein the filter unit, in the closed position, is held on the sterile container under prestress.

22. A container according to claim 20, further comprising a sealing element for mounting the filter unit in a gastight manner.

23. A container according to claim 20, further comprising:
a pressure-relief valve, disposed in such a way that in a basic position it adopts a closed position and that it adopts a flow-permitting position when a pressure in the vicinity of the sterile container exceeds a pressure in the sterile container by a predetermined pressure difference.

24. A container according to claim 20, further comprising an inflow edge, is disposed on an outer side of the lid, facing away from the gas exchange opening and sloping downward toward an outside relative to a lid plane.

25. A container according to claim 20, wherein the lid has at least one spacer element for stacking a further sterile container on the sterile container, so that gas exchange through the gas exchange opening is possible with stacked sterile containers.

26. A container according to claim 20, wherein the sterile filter is a long-term filter made from polytetrafluoroethylene (PTFE).

* * * * *

UNITED STATES PATENT AND TRADEMARK OFFICE
CERTIFICATE OF CORRECTION

PATENT NO.        : 7,381,385 B2                                             Page 1 of 1
APPLICATION NO.   : 10/846853
DATED             : June 3, 2008
INVENTOR(S)       : Gleichauf et al.

It is certified that error appears in the above-identified patent and that said Letters Patent is hereby corrected as shown below:

Column 8, line 55 is corrected to read: --element being nonreleasably connectable to one another,--

Column 9, line 12 is corrected to read: --an inflow edge disposed on an outer side of the lid facing--

Signed and Sealed this

Twelfth Day of August, 2008

JON W. DUDAS
*Director of the United States Patent and Trademark Office*